US010835538B2

(12) United States Patent
Averback

(10) Patent No.: US 10,835,538 B2
(45) Date of Patent: Nov. 17, 2020

(54) METHOD OF TREATING BENIGN PROSTATIC HYPERLASIA WITH ANTIBIOTICS

(71) Applicant: Nymox Corporation, Nassau (BS)

(72) Inventor: Paul Averback, Nassau (BS)

(73) Assignee: NYMOX CORPORATION, Nassau (BS)

(*) Notice: Subject to any disclaimer, the term of this patent is extended or adjusted under 35 U.S.C. 154(b) by 21 days.

(21) Appl. No.: 15/938,920

(22) Filed: Mar. 28, 2018

(65) Prior Publication Data
US 2019/0298731 A1    Oct. 3, 2019

(51) Int. Cl.
| A61K 31/546 | (2006.01) |
| A61P 13/08 | (2006.01) |
| A61K 31/343 | (2006.01) |
| A61K 31/407 | (2006.01) |
| A61K 31/4164 | (2006.01) |
| A61K 31/4178 | (2006.01) |
| A61K 31/43 | (2006.01) |
| A61K 31/4375 | (2006.01) |
| A61K 31/4709 | (2006.01) |
| A61K 31/496 | (2006.01) |
| A61K 31/5383 | (2006.01) |
| A61K 31/545 | (2006.01) |
| A61K 31/65 | (2006.01) |
| A61K 31/665 | (2006.01) |
| A61K 31/7036 | (2006.01) |
| A61K 31/7048 | (2006.01) |
| A61K 38/10 | (2006.01) |
| A61K 38/13 | (2006.01) |

(52) U.S. Cl.
CPC .......... *A61K 31/546* (2013.01); *A61K 31/343* (2013.01); *A61K 31/407* (2013.01); *A61K 31/4164* (2013.01); *A61K 31/4178* (2013.01); *A61K 31/43* (2013.01); *A61K 31/4375* (2013.01); *A61K 31/4709* (2013.01); *A61K 31/496* (2013.01); *A61K 31/5383* (2013.01); *A61K 31/545* (2013.01); *A61K 31/65* (2013.01); *A61K 31/665* (2013.01); *A61K 31/7036* (2013.01); *A61K 31/7048* (2013.01); *A61K 38/10* (2013.01); *A61K 38/13* (2013.01); *A61P 13/08* (2018.01)

(58) Field of Classification Search
CPC combination set(s) only.
See application file for complete search history.

(56) References Cited

U.S. PATENT DOCUMENTS

| 4,547,489 A | 10/1985 | Goldstein et al. |
| 6,296,847 B1 | 10/2001 | Gokcen et al. |
| 6,924,266 B2 | 8/2005 | Averback |
| 7,241,738 B2 | 7/2007 | Averback et al. |
| 7,317,077 B2 | 1/2008 | Averback et al. |
| 7,408,021 B2 | 8/2008 | Averback et al. |
| 7,745,572 B2 | 6/2010 | Averback et al. |
| 8,067,378 B2 | 11/2011 | Averback et al. |
| 8,293,703 B2 | 10/2012 | Averback et al. |
| 8,569,446 B2 | 10/2013 | Averback et al. |
| 8,716,247 B2 | 5/2014 | Averback et al. |
| 2016/0215031 A1 | 7/2016 | Averback |
| 2016/0361380 A1 | 12/2016 | Averback |
| 2017/0020957 A1 | 1/2017 | Averback |
| 2017/0360885 A1 | 12/2017 | Averback |
| 2018/0064785 A1 | 3/2018 | Averback |

FOREIGN PATENT DOCUMENTS

| WO | 90/08555 A1 | 8/1990 | |
| WO | WO-2007149312 A2 * | 12/2007 | ............. A61K 8/606 |

OTHER PUBLICATIONS

McClellan et al., Topical Metronidazole A Review of its Use in Rosacea, 2000, Am J Clin Dermatol, 1(3), pp. 191-199 (Year: 2000).*
Ricciotti et al., Prostaglandins and Inflammation, 2011, Arterioscler Thromb Vasc Biol., 31(5), pp. 986-1000 (Year: 2011).*
Altschul et al., Basic Local Alignment Search Tool, J. Mol. Biol., 1990, pp. 403-410, vol. 215.
AUA Practice Guidelines Committee, Chapter 1, AUA Guideline on Management of Benign Prostatic Hyperplasia. Diagnosis and Treatment Recommendations, The Journal of Urology, Aug. 2003, pp. 530-547, vol. 170.
Auffenberg et al., Established Medical Therapy for Benign Prostatic Hyperplasia, Urol. Clin. North Am. 2009, pp. 443-459, vol. 36.
Carrillo et al., The Multiple Sequence Alignment Problem in Biology, SIAM J. Appl. Math., Oct. 1988, pp. 1073-1082, vol. 48(5).
Cindolo et al., Drug Adherence and Clinical Outcomes for Patients Under Pharmacological Therapy for Lower Urinary Tract Symptoms Related to Benign Prostatic Hyperplasia: Population-based Cohort Study, European Urology, 2015, pp. 418-425, vol. 68.
Couder et al., Synthesis and biological activities of ψ(CH2NH) pseudopeptide analogues of the C-terminal hexapeptide of neurotensin, Int. J. Peptide Protein Res., 1993, pp. 181-184, vol. 41.
Dalpozzo et al., H-Gly-Hisψ(NHC0)Lys-OH, partially modified retro-inverso analogue of the growth factor glycyl-L-histidyl-L-lysine with enhanced enzymatic stability, Int. J. Peptide Protein Res., 1993, pp. 561-566, vol. 41.

(Continued)

*Primary Examiner* — Kortney L. Klinkel
*Assistant Examiner* — Tori Strong
(74) *Attorney, Agent, or Firm* — Pillsbury Winthrop Shaw Pittman, LLP

(57) ABSTRACT

Disclosed are methods of improving the symptoms of mammals suffering from BPH using compositions containing one or more antibiotics. The method includes, but is not limited to, administering at least one antibiotic in one or more courses of treatment by one or more administration routes selected from intramuscularly, orally, intravenously, intrathecally, intratumorally, intranasally, topically, and transdermally, either alone or with a carrier to a mammal in need thereof.

15 Claims, No Drawings

Specification includes a Sequence Listing.

(56) References Cited

OTHER PUBLICATIONS

Dayhoff et al., A Model of Evolutionary Change in Proteins, Atlas of Protein Sequence and Structure, 1978, pp. 345-352, vol. 5, Supp.3 for the PAM250 comparison matrix.
Devereux et al., A comprehensive set of sequence analysis programs for the VAX, Nucleic Acids Research, 1984, pp. 387-395, vol. 12(1).
Ede et al., Conformationally constrained peptide analogs with hypoglycaemic activity, Peptides Chemistry and Biology, Proceedings of the Twelfth American Peptide Symposium, Jun. 16-21, 1991, pp. 268-270, Cambridge, MA, USA.
Freireich et al., Quantitative Comparison of Toxicity of Anticancer Agents in Mouse, Rat, Hamster, Dog, Monkey, and Man, Cancer Chemotherapy Reports, May 1966, pp. 219-244, vol. 50(4).
Henikoff et al., Amino acid substitution matrices from protein blocks, Proc. Natl. Acad. Sci. USA, Nov. 1992, pp. 10915-10919, vol. 89.
Hutchison et al., The Efficacy of Drugs for the Treatment of LUTS/BPH, A Study in 6 European Countries, European Urology, 2007, pp. 207-216, vol. 51.
Lee et al., Intrinsic and Extrinsic Factors Controlling Benign Prostatic Growth, The Prostate, 1997, pp. 131-138, vol. 31.
Lukacs et al., Management of Lower Urinary Tract Symptoms Related to Benign Prostatic Hyperplasia in Real-life Practice in France: A Comprehensive Population Study, European Urology, 2013, pp. 493-501, vol. 64.
McConnell et al., The Effect of Finasteride on the Risk of Acute Urinary Retention and the Need for Surgical Treatment Among Men with Benign Prostatic Hyperplasia, the New England Journal of Medicine, Feb. 26, 1998, pp. 557-563, vol. 338(9).
Oelke et al., EAU Guidelines on the Treatment and Follow-up of Non-neurogenic Male Lower Urinary Tract Symptoms Including Benign Prostatic Obstruction, European Urology, 2013, pp. 118-140, vol. 64.
Creighton, Thomas E., Proteins—Structure and Molecular Properties, 2nd Ed., 1993, W. H. Freeman and Company, New York, USA.
Rattan et al., Protein Synthesis, Posttranslational Modifications, and Aging, Annals New York Academy of Sciences, 1992, pp. 48-62, vol. 663.
Roehrborn et al., Corrigendum to "The Effects of Combination Therapy with Dutasteride and Tamsulosin on Clinical Outcomes in Men with Symptomatic Benign Prostatic Hyperplasia: 4-Year Results from the CombAT Study", European Urology, 2010, p. 801, vol. 58.
Roehrborn et al., Influence of baseline variables on changes in International Prostate Symptom Score after combined therapy with dutasteride plus tamsulosin or either monotherapy in patients with benign prostatic hyperplasia and lower urinary tract symptoms: 4-year results of the CombAT study, BJUI Int., 2014, pp. 623-635, vol. 113.
Scientific Tables, 7th Ed., 1970, pp. 537-538, Geigy Pharmaceuticals, Ardsley, NY, USA.
Seifter et al., Analysis for Protein Modifications and Nonprotein Cofactors, Methods in Enzymology, 1990, pp. 626-646, vol. 182.
Simon et al., Peptoids: A modular approach to drug discovery, Proc. Natl. Acad. Sci. USA, Oct. 1992, pp. 9367-9371, vol. 89.
Sisto et al., Biologically active retro-inverso analogs of thymopentin, Peptides—Chemistry, Structure and Biology, Proceedings of the Eleventh American Peptide Symposium, Jul. 9-14, 1989, La Jolla, CA, USA, pp. 772-773.
Smith et al., Tritiated D-ala1-Peptide T Binding: A Pharmacologic Basis for the Design of Drugs Which Inhibit HIV Receptor Binding, Drug Development Research, 1988, pp. 371-379, vol. 15.
Von Heijne, Gunnar, Sequence Analysis in Molecular Biology, 1987, pp. 123-139, Academic Press, New York, NY, USA.
Wold, Finn, Posttranslational Protein Modifications: Perspectives and Prospectives, Posttranslational Covalent Modification of Proteins, B. C. Johnson, Ed., 1983, pp. 1-12, Academic Press, New York, NY, USA.
International Search Report and Written Opinion of the International Searching Authority dated Jul. 4, 2019 issued in corresponding International Application No. PCT/US2019/024319.
Annie Hutchison et al., "The Efficacy of Drugs for the Treatment of LUTS/BPH, A Study in 6 European Countries", European Urology, vol. 51, No. 1, (2007), pp. 207-216.
Yoon-Soo Kyung et al., "Changes in Serum Prostate-Specific Antigen after Treatment with Antibodies in Patients with Lower Urinary Tract Symptoms/Benign Prostatic Hyperplasia with Prostatitis", International Neurology Journal, vol. 14, No. 2, (2010), pp. 100-104.
Neal Shore et al., "The potential for NX-1207 in benign prostatic hyperplasia: an update for clinicians", Therapeutic Advances in Chronic Disease, (2011) 2(6) pp. 377-383.
International Preliminary Report on Patentability dated Jul. 9, 2020 issued in corresponding International Application No. PCT/US2019/024319 (13 pgs).

* cited by examiner

METHOD OF TREATING BENIGN PROSTATIC HYPERLASIA WITH ANTIBIOTICS

SEQUENCE LISTING

The instant application contains a Sequence Listing which has been submitted electronically in ASCII format and is hereby incorporated by reference in its entirety. Said ASCII copy, created on May 15, 2018, is named 063307-0458312_SL.txt and is 749 bytes in size.

BACKGROUND

1. Field of the Embodiments

The embodiments include methods of treating benign prostatic hyperplasia using compositions that include at least one antibiotic. Other embodiments include methods of treating benign prostatic hyperplasia using compositions that include at least one antibiotic, one or more compounds based on small peptides, and a pharmaceutically acceptable carrier.

2. Description of Related Art

Benign Prostatic Hyperplasia (BPH) is a histologic diagnosis that refers to the nonmalignant proliferation of smooth muscle and epithelial cells of the prostate. Lee C, et al., "Intrinsic and extrinsic factors controlling benign prostatic growth," Prostate, 1997; 31:131-138; Auffenberg G B, et al., "Established medical therapy for benign prostatic hyperplasia," *Urol Clin North Am.*, 2009; 36:443-459. The exact etiology is unknown. The progression of BPH can lead to benign prostatic enlargement (BPE), which is determined by the size of the prostate (pathologic). Approximately 50% of men with histologic BPH develop BPE. BPE may eventually cause bladder outlet obstruction (BOO), which is also termed benign prostatic obstruction (BPO) if associated with BPE. BOO and BPO are determined with urodynamic measures.

The development of BPH is a phenomenon of aging men. The prostate weighs a few grams at birth and at puberty undergoes an androgen-induced growth reaching the adult size of 20 g by the second decade of life. The prostate typically remains stable in weight and histological characteristics for about 25 years. In the fifth decade a second spurt of growth begins in most men. This second growth phase originates in the periurethral area of the gland as a localized proliferation of cells. Growth and enlargement may progress to compress the remaining normal gland, result in a major increase in gland size, and cause urinary and/or rectal obstruction.

Benign prostatic hyperplasia (BPH) is associated with difficulties in lower urinary tract function. These symptoms include problems such as the sensation of incomplete emptying of the bladder after urination; the need to urinate frequently; stopping and starting several times during urination; difficulty to postpone urination; weak urinary stream; the need to strain and push during urination; and the need to urinate during the night after going to sleep. Diagnosis of prostate conditions involves considerations of all possible conditions in the differential diagnosis, eg, cancer, infection, benign enlargement, etc. and that evaluation requires tests and assessments done by qualified clinicians using techniques and data from history, physical examination, imaging, laboratory analyses, and specialized testing such as urinary flow rates and other functional tests, endoscopy, biopsies, and clinical responses to interventions and drugs.

The diagnosis of prostatitis involves careful history and physical examination, analyses and cultures of urine and prostatic secretions, and often therapeutic responses to courses of antibiotics. The spectrum of symptoms from prostatitis can include nonspecific symptoms as well as more typical symptoms of pain and signs of inflammation. The nonspecific symptoms can include urgency, frequency, nocturia, and disorders of urination that are also found in BPH. Antibiotics and anti-infectives have not been considered an accepted treatment for BPH.

BPH is believed to arise from an inner set of prostatic ducts and glands that reside within or adjacent to the urethral wall. The initial lesions are usually comprised of a tiny mass of loose connective tissue stroma lacking glandular components. However, as the nodule develops and grows, glandular tissue predominates. Once the hyperplastic process is initiated, all elements of the normal prostate (stromal, muscular, and glandular) participate to various degrees in the progressive growth. Determinations of the relative amounts of these tissues in patients with BPH have shown that the amount of fibromuscular tissue far exceeds the amount of glandular or epithelial tissue. The fibromuscular stroma composes approximately 45% of the volume of the normal prostate as opposed to approximately 60% in the hyperplastic gland.

Hypertrophy of the stromal and glandular (epithelial) components may occur alone or together. The variable response is evidenced by the nature of the nodules and theft phases of development. The glands in the hyperplastic nodules seem to have the ability to bud and form new ducts and acini. Stromal nodules rarely reach large size, while clinically significant growths usually have large glandular components. Prostatic enlargement is often described in terms of enlargement of a glandular organ; however, smooth muscle is also an important component. The prostatic capsule possesses an even higher proportion of muscular tissue.

A primary symptom of benign enlargement of the prostate is urinary obstruction. Urethral obstruction occurs as a result of compression or elongation of the urethra. Benign nodular hyperplasia alone may cause urinary obstruction by physically obstructing the urethra or by interfering with the muscle or nerves supplying the urinary sphincter. The exact location of the nodular hyperplasia determines the speed and intensity of obstructive symptoms. A small strategically located nodule may cause more obstruction than larger more lateral hypertrophies that remain within the prostatic capsule. Hematuria is a common symptom of BPH because prostatic hypertrophy is a vascular growth with dilated veins on the urethral surface. Other irritative symptoms include increased frequency of urination and severe urgency that compels the passage of urine with a minimum of warning. The most serious complication of prostatic, hypertrophy is the effect the obstruction has on the upper urinary tract. The obstruction may lead to hydronephrosis, severe renal damage, and potentially fatal uremia.

There are a number of treatments currently available for BPH, See, Chpt. 1, Guidelines on the Management of Benign Prostatic Hyperplasia (BPH), American Urological Association Education and Research, Inc., (2001); Oelke M, et al., European Association of Urology, *Eur. Urol.* 2013 July; 64(1):118-40. The guidelines discuss treatment options varying from watchful waiting (WW), for men presenting with symptoms but are not bothered enough to need medication or surgical intervention, to drug treatments, to surgical intervention. If medical treatment is needed, medicines such as α-blockers, or alpha-adrenergic antagonists (e.g., Alfuzosin, Doxazosin, Tamsulosin, Terazosin, Silodosin), 5-α-reductase inhibitors 5ARIs (Dutasteride, Finasteride), antimuscarinics (anticholinergics), a PDE5 inhibitor (tadalafil), and combinations therefore can be used. Minimally invasive therapies include transurethral needle ablation (TUNA) and transurethral microwave thermotherapy (TUMT). Invasive surgical procedures include open prostatectomy; transurethral holmium laser ablation (HoLAP) or laser enucleation (HoLEP), holmium laser resection (HoLRP), photoselective vaporization (PVP), transurethral incision of the prostate (TUIP), transurethral vaporization of the prostate (TUVP), and transurethral resection of the prostate (TURP).

Prostatectomy is the currently accepted procedure for relieving bladder neck obstruction due to BPH. The goals of surgical treatment are to reverse and eliminate the effects of urinary obstruction such as renal failure, stone formation, and infection. Additionally, it is desirable to improve the quality of the patient's life by allowing him to void at normal intervals with good control and to allow normal sexual function. The indications for surgical prostatectomy include: male under 70 years of age; normal kidneys; fairly healthy bladder; marked enlargement of the prostate on rectal examination; decided urethral obstruction: over four ounces of residual urine; and symptoms of urination frequency, pain, tenesmus, burning, attacks of urethral fever, epididymitis, and hematuria. When patients have enough bladder neck obstruction to produce severe symptoms and are good surgical risks, removal of the obstructive prostatic tissue is usually advised by the suprapubic, retropubic, perineal, or transurethral route.

The rates of mortality for open surgical prostatectomy are essentially comparable for the various techniques, with the risk of mortality fluctuating around 1%. The risk of death is less in patients subjected to TURF. Patients with recognized renal failure are regarded as poor risks for prostatectomy. Men over 80 years of age are at greater risk as the mortality rate for TURP increases.

It is well known that castration effectively prevents BPH. The prostate, whether enlarged or normal, undergoes atrophy after orchiectomy and changes into a small tough fibrous mass in which there are only remnants of glandular tubules and ducts. Although this procedure was used at the turn of the century, it was abandoned in favor of excision of the obstructing tissue. Most attempts at controlling prostatic enlargement have centered on the administration of hormonal steroids and are based on the concept that castration results in symptomatic improvement and reduction in prostatic size by removal of the major source of androgenic stimulation. Specific antiandrogenic therapies have been directed at the inhibition of prostatic growth by preventing the onset of obstructive urinary symptoms or by inducing prostatic regression and involution, thereby relieving the symptoms of obstruction.

Efforts aimed at depriving the prostate of androgenic stimulation have taken a variety of approaches including estrogen therapy suppression of luteinizing hormone (LH) and antiandrogen therapy. Estrogen therapy for BPH is based on the fact that estrogens, in appropriate dosages, reduce the levels of circulating testosterone. Medical forms of therapy aimed at controlling BPH include the use of antiandrogens which inhibit prostatic growth yet do not produce deleterious side effects. Antiandrogens have been shown to competitively inhibit the binding of dihydrotestosterone to cellular receptors and to reduce testosterone concentrations in the male to castrate levels. However, once the antiandrogens are discontinued, the hyperplasia returns. Therefore, patients undergoing this type of therapy look forward to a lifetime of medication with the attendant undesirable side-effects of antiandrogenic therapy. Commonly reported side effects of this therapy include breast enlargement, nipple tenderness, loss of libido, impotence, and acne.

Testosterone is a prohormone that is converted to dihydrotestosterone in the prostate by the action of 5-α-reductase. As a result, the enzyme 5-α-reductase has been proposed as a target for the action of suicide inhibitors to reduce the levels of dihydrotestosterone. This has been shown to mediate benign prostatic enlargement. Steroid diazoketones have been shown to be unique analogs of the natural substrates for the enzyme 5-α-reductase and inhibit the enzyme's catalytic activity by forming covalent bonds in or near the enzyme's active site through diazonium alkylation.

Ketoconazole is an imidazole derivative that has been shown to be a potent inhibitor of gonadal and adrenal testosterone production. Ketoconazole does not appear to affect the pituitary in its secretion of LH; however, it does inhibit cholesterol synthesis, result in clinical reductions of adrenal and gonadal androgen levels, and is of low toxicity. The hormonal changes produced by the administration of ketoconazole are dose-dependent and fully reversible. The drug has been shown to be useful in clinical conditions that may benefit from inhibition of gonadal or adrenal steroid production, Ketoconazole has been shown to be a potent inhibitor of testosterone synthesis and may be of therapeutic benefit in the management of BPH. Potential side effects of ketoconazole therapy include decreased libido, impotence, gynecomastia, and hypogonadism.

Ornithine decarboxylase is an enzyme that is involved in the biosynthesis of the polyamines putrescine, spermidine, and spermine. These polyamines are thought to be involved in enhanced cellular growth and replication. Elevated levels of these polyamines are found in the prostate and other glands that are undergoing rapid proliferation. Upon the synthesis of potent suicide inhibitors of ornithine decarboxylase, such as DL-α-difluoromethyl-ornithine (DFMO), the prostatic levels of ornithine decarboxylase have been shown to be markedly reduced with the subsequent depletion of putrescine and spermidine. In animals, administration of the suicide inhibitor of ornithine decarboxylase, DFMO, has resulted in the inhibition of the growth of the prostate. Additionally, in tissue culture, DFMO inhibits DNA synthesis and slows the proliferation of human prostate adenoma cells. This compound may find application in the treatment of prostatic adenoma.

Additional attempts at the medical management of BPH as an alternative mode of therapy to surgical techniques have included the use of potent LHRH (luteinizing hormone releasing hormone) agonists which block testicular production of testosterone by inhibiting pituitary release of gonadotropins. The primary effect of LHRH agonists in humans is the reduction of serum testosterone levels. Leuprolide and nafarelin acetate have been shown to reduce circulating levels of androgens and estrogens in males to castrate levels within three weeks. These compounds in continuous and therapeutic doses desensitize the pituitary and block the release of sex steroid hormones. The degree of testosterone suppression achieved with potent LHRH agonists has been shown to be effective in the treatment of obstructive benign prostatic hypertrophy. Drawbacks to this form of therapy include the need to maintain medication indefinitely as androgenic suppression is reversible with subsequent regrowth of hyperplastic tissue. Furthermore, side effects include impotence, decreased libido, hot flashes, and may include an initial increase in obstructive symptoms.

Other efforts to prevent or treat BPH by nonsurgical means include the use of neuro pharmacological agents such as α-1-adrenergic blocking agents. Prazosin, Hytrin, phentolamine, and ketanserin are anti-adrenergic drugs aimed at relaxation of the urinary sphincter mechanism. The pharmacologic treatment of BPH with α-adrenergic blockers provides a means for helping a large number of patients with prostatic enlargement in whom surgical intervention is not deemed necessary or has to be postponed. Various α-adrenergic blocking agents have been employed in the treatment of BPH and include the compounds phenoxybenzarnine (potential mutagen), prazosin (Minipres), phentolamine (Regitine), nicergoline (Sermion), terazosin (Hytrin), and thymoxamine. Side effects are present in approximately 30% of the patients treated with phenoxybenzamine for BPH and include hypotension, dizziness, faintness, tachycardia, weakness, and retrograde or absent ejaculation. In about 10% of all cases treated, the side effects cannot be tolerated and therapy has to be abandoned. Prazosin and Hytrin seem to produce fewer side effects. The possibility of cerebral hypotension or schema appears to be a contraindication for these agents. Rapidly acting intravenous blockers such as phentolamine must be used with caution particularly in older age groups. However, nicergoline is thought to have a beneficial effect upon the cerebral circulation.

Pharmacologic evidence has shown that prostatic size in animals can be reduced subsequent to the lowering of serum cholesterol. Polyene macrolides have been shown to be effective and potent hypocholesterolemic agents. The polyene macrolides as a group have a specific physico-chemical affinity for sterols and sterol containing cellular membranes. Based upon toxicity studies in animals, polyene macrolides have been shown to reduce serum testosterone levels, inhibit testicular function, and induce alterations in prostatic histology. The polyene macrolide antifungal agents candicidin and amphotericin B have been shown to produce reductions in the volume of the prostate gland, but human clinical trials have not shown a reduction in the number of patients requiring surgical intervention for obstructive symptoms due to BPH. U.S. Pat. No. 6,296,847, the disclosure of which is incorporated by reference herein in its entirety.

Over the past 40 years, many attempts have been made to medically manage this disease. The interpretation of the results of these attempts has been complicated by the fact that patients with symptoms attributable to BPH often experience temporary improvement or remission of voiding symptoms following diagnostic instrumentation alone. The efficacy of treatment of BPH with pharmaceuticals often is measured in terms of mean improvement in International Prostate Symptom Score (IPSS) from baseline. Most reported studies show, at best, a mean improvement in IPSS from the use of pharmaceuticals (alone or in combination) to be within the range of from about 2 to at best 6 points in 12 months or longer. Roehrbom, et al., "Influence of baseline variables on changes in . . . ," *GJUI Int, Vol.* 113, pp 623-635 (2014); Hutchison, et al., "The Efficacy of Drugs for the Treatment of LUTS/BPH, A Study in 6 European Countries," *European Urology*, Vol. 51, pp 207-216 (2007). It is generally accepted that the averages of the mean improvement in IPSS from the FDA-approved conventional oral BPH medications ranges from about 3 to about 5.

Some peptide-based agents are known to have the ability to destroy and hence either facilitate the removal of or inhibit the further growth of harmful or unwanted cells and tissue such as benign hyperplastic prostate cells and tissue. These agents are disclosed in U.S. Pat. Nos. 6,924,266; 7,241,738; 7,317,077; 7,408,021; 7,745,572; 8,067,378; 8,293,703; 8,569,446; and 8,716,247; and U.S. Patent Application Publication Nos. 2017/0360885; 2017/0020957; 2016/0361380; and 2016/0215031, the disclosures of each of which are incorporated by reference herein in their entirety. One such agent is known as Fexapotide Triflutate.

There exists a need for treatments that can improve the symptoms of BPH without the risks and side effects of conventional drug therapies, or surgical intervention.

Throughout this description, including the foregoing description of related art, any and all publicly available documents described herein, including any and all U.S. patent published patent applications, are specifically incorporated by reference herein in their entirety. The foregoing description of related art is not intended in any way as an admission that any of the documents described therein, including pending U.S. patent applications, are prior art to the present disclosure. Moreover, the description herein of any disadvantages associated with the described products, methods, and/or apparatus, is not intended to limit the embodiments. Indeed, aspects of the embodiments may include certain features of the described products, methods, and/or apparatus without suffering from their described disadvantages.

SUMMARY OF THE EMBODIMENTS

There remains a need for new, less toxic, and less frequent (e.g., avoiding the need to take medications daily or weekly) treatments for BPH, and for improving the quality of life for patients suffering from BPH.

This disclosure is premised in part on the discovery that antibiotics, when administered alone or in combination with certain peptides, including a specific peptide described by the amino acid sequence Ile-Asp-Gln-Gln-Val-Leu-Ser-Arg-Ile-Lys-Leu-Glu-Ile-Lys-Arg-Cys-Leu, (SEQ ID NO:1), (Fexapotide Triflutate or "FT") are capable of treating BPH as evidenced by a mean improvement in IPSS within the range of from about 4.0 to about 8.0 points within the first year.

This disclosure also is premised in part on the discovery that antibiotics either alone or in combination with FT is effective in improving the urinary peak flow rate (Qmax) in men suffering from BPH. The mean improvement in Qmax can be within the range of from about 1.0 to about 4.0.

The antibiotics and optionally FT can be administered together or separately, and can be administered orally, intramuscularly, orally, intravenously, intraperitoneally, intracerebrally (intraparenchymally), intracerebroventricularly, intratumorally, intralesionally, intradermally, intrathecally, intranasally, intraocularly, intraarterially, topically, transdermally, via an aerosol, infusion, bolus injection, implantation device, sustained release system etc.

Both the foregoing general description and the following detailed description are exemplary and explanatory and are intended to provide further explanation of the embodiments as claimed. Other objects, advantages, and features will be readily apparent to those skilled in the art from the following detailed description of the embodiments.

DETAILED DESCRIPTION OF THE PREFERRED EMBODIMENTS

Before the embodiments are described, it is understood that this invention is not limited to the particular methodology, protocols, cell lines, vectors, and reagents described, as these may vary. It also is to be understood that the terminology used herein is for the purpose of describing particular embodiments only, and is not intended to limit the scope of the present embodiments which will be limited only by the appended claims.

Terms and phrases used herein are defined as set forth below unless otherwise specified. Throughout this description, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

The term antibiotic as used herein denotes antibiotics, antiseptics and disinfectants. Examples of antibiotics include erythromycin ethyl succinate, erythromycin ethylcarbonate, erythromycin glucoheptanoate, erythromycin stearate, erythromycin lauryl sulfate propionate, erythromycin lactobionate, triacetyl oleandomycin, oleandomycin phosphate, amikacin sulfate, bekanamycin sulfate, aminodeoxykanamycin, kanamycin monosulfate, tobramycin, acetyl kitasamycin, kitasamycin, kitasamycin succinate, kitasamycin tartarate, chloramphenicol, chloramphenicol alginine succinate, chloramphenicol sodium succinate, chloramphenicol stearate, chloramphenicol morpholinoacetate, chloramphenicol palmitate, chloramphenicol stearoylglycolate, chloramphenicol sulfate morpholinoacetate, colistin hydrochloride, colistin, colistin sodium methane sulfonate, colistin sulfate, josamycin, josamycin propionate, dihydrostreptomycin hydrochloride, dihydrostreptomycin sulfate, compound streptomycin, streptomycin hydrochloride, streptomycin calcium chloride hydrochloride, streptomycin sulfate, streptomycin isoniazone sulfate, cephacetrile sodium, cephazolin sodium, cephapyrin sodium, cephalexin, cephaglycin, cephalothin sodium, cephaloridine, ceftezol sodium, cephradine, oxytetracycline hydrochloride, oxytetracycline, oxytetracycline calcium, chlorotetracycline hydrochloride, chlorotetracycline, tetracycline hydrochloride, rolitetracycline nitrate, tetracycline L-methylene-lysine, tetracycline methaphosphate, rolitetracycline, dimethylchlorotetracycline hydrochloride, dimethylchlorotetracycline, doxycycline hydrochloride, minocycline hydrochloride, metacycline hydrochloride, actinomycin D, azalomycin F, enbiomycin sulfate, enramycin hydrochloride, aureothricin, capreomycin sulfate, carzinophilin, carbomycin, gramicidin, gramicidine S hydrochloride, griseofulvin, chromomycin A3, gentamicin sulfate, cycloserin, sarkomycin, siccanin, dibekacin sulfate, acetylspiramycin, spiramycin, spectinomycin hydrochloride, daunorubicin hydrochloride, doxorubicin hydrochloride, trichomycin, nystatin, neocarzinostatin, novobiocin calcium, novobiocin sodium, viomycin sulfate, bacitracin, variotin, paromomycin sulfate, pimaricin, pyrrolnitrin, fusidate sodium, fradiomycin palmitate, fradiomycin sulfate, bleomycin hydrochloride, bleomycin sulfate, ampicillin, ampicillin sodium, imipenem, metronidazole, talampicillin hydrochloride, carbenicillin sodium, carbenicillin indanyl sodium, carbenicillin phenyl sodium, phenoxymethylpenicillin, phenoxymethylpenicillin potassium, phenoxymethylpenicillin calcium, phenoxymethylpenicillin benzathine, penicillin potassium, penicillin sodium, penicillin procaine, benzylpenicillin potassium, benzylpenicillin sodium, benzylpenicillin procaine, benzylpenicillin benzathine, compound penicillin potassium, compound benzylpenicillin potassium, compound benzylpenicillin sodium, compound benzylpenicillin benzathine, clindamycin hydrochloride, clindamycin palmitate hydrochloride, lincomycin hydrochloride, amoxicillin, oxacillin sodium, cloxacillin sodium, cyclacillin, dicloxacillin sodium, sulbenicillin sodium, pivmecillinam hydrochloride, phenethicillin potassium, flucloxacillin sodium, propicillin potassium, hetacillin potassium, methicillin sodium, pentamycin, polymyxin B sulfate, mitomycin C, maridomycin propionate, mikamycin, midecamycin, rifampicin, ribostamycin sulfate, pyrrolenitrin, actinomycin, bleomycin, daunorubicin, doxorubicin and neocarzinostatin. Other antibiotics include fluoroquinolone antibiotics such as ciprofloxacin (Cipro), gemifloxacin (Factive), levofloxacin (Levaquin), moxifloxacin (Avelox), norfloxacin (Noroxin), and ofloxacin (Floxin). As the antiseptics and disinfectants, it is preferred to use dyestuff/medical preparations such as acrinol or acriflavine, etc., furan medical preparations such as nitrofurazone, etc., cationic soap medical preparations such as benzalkonium chloride or benzethonium chloride, etc., cyclohexidine and povidone-iodine. It generally is preferred to use a combination of two or more antibiotics.

Amino acids and amino acid residues described herein may be referred to according to the accepted one or three-letter code provided in the table below.

TABLE 1

| Three-Letter Amino Acid | One-Letter Symbol | Symbol |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

Fexapotide Triflutate ("FT"), as it is used herein, denotes a 17-mer peptide having the amino acid sequence: Ile-Asp-Gln-Gln-Val-Leu-Ser-Arg-Ile-Lys-Leu-Glu-Ile-Lys-Arg-Cys-Leu (SEQ ID NO. 1). FT is disclosed in U.S. Pat. Nos. 6,924,266; 7,241,738; 7,317,077; 7,408,021; 7,745,572; 8,067,378; 8,293,703; 8,569,446; and 8,716,247, and U.S. Patent Application Publication Nos. 2017/0360885; 2017/0020957; 2016/0361380; and 2016/0215031. The disclosures of these patents and published applications are incorporated by reference herein in their entirety.

FT is represented by:

```
SEQ ID NO. 1:
IDQQVLSRIKLEIKRCL
or

Ile-Asp-Gln-Gln-Val-Leu-Ser-Arg-Ile-Lys-Leu-Glu-
Ile-Lys-Arg-Cys-Leu.
```

The term "fragment" refers to a protein or polypeptide that consists of a continuous subsequence of the amino acid sequence of a protein or peptide and includes naturally occurring fragments such as splice variants and fragments resulting from naturally occurring in vivo protease activity. Such a fragment may be truncated at the amino terminus, the carboxy terminus, and/or internally (such as by natural splicing). Such fragments may be prepared with or without an amino terminal methionine. The term "fragment" includes fragments, whether identical or different, from the same protein or peptide, with a contiguous amino acid sequence in common or not, joined together, either directly or through a linker. A person having ordinary skill in the art will be capable of selecting a suitable fragment for use in the embodiments without undue experimentation using the guidelines and procedures outlined herein.

The term "variant" refers to a protein or polypeptide in which one or more amino acid substitutions, deletions, and/or insertions are present as compared to the amino acid sequence of an protein or peptide and includes naturally occurring allelic variants or alternative splice variants of an protein or peptide. The term "variant" includes the replacement of one or more amino acids in a peptide sequence with a similar or homologous amino acid(s) or a dissimilar amino acid(s). There are many scales on which amino acids can be ranked as similar or homologous. (Gunnar von Heijne, Sequence Analysis in Molecular Biology, p. 123-39 (Academic Press, New York, N.Y. 1987.) Preferred variants include alanine substitutions at one or more of amino acid positions. Other preferred substitutions include conservative substitutions that have little or no effect on the overall net charge, polarity, or hydrophobicity of the protein. Conservative substitutions are set forth in Table 2 below.

TABLE 2

Conservative Amino Acid Substitutions

| Basic: | arginine |
| | lysine |
| | histidine |
| Acidic: | glutamic acid |
| | aspartic acid |
| Uncharged Polar: | glutamine |
| | asparagine |
| | serine |
| | threonine |
| | tyrosine |
| Non-Polar: | phenylalanine |
| | tryptophan |
| | cysteine |
| | glycine |
| | alanine |
| | valine |
| | praline |
| | methionine |
| | leucine |
| | isoleucine |

Table 3 sets out another scheme of amino acid substitution:

TABLE 3

| Original Residue | Substitutions |
|---|---|
| Ala | gly; ser |
| Arg | lys |
| Asn | gln; his |
| Asp | glu |
| Cys | ser |
| Gln | asn |
| Glu | asp |
| Gly | ala; pro |
| His | asn; gln |
| Ile | eu; val |
| Leu | ile; val |
| Lys | arg; gln; glu |

TABLE 3-continued

| Original Residue | Substitutions |
|---|---|
| Met | leu; tyr; ile |
| Phe | met; leu; tyr |
| Ser | thr |
| Thr | ser |
| Trp | tyr |
| Tyr | trp; phe |
| Val | ile; leu |

Other variants can consist of less conservative amino acid substitutions, such as selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected to have a more significant effect on function are those in which (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; or (e) a residue having a bulky side chain, e.g., phenylalanine, is substituted for (or by) one not having such a side chain, e.g., glycine. Other variants include those designed to either generate a novel glycosylation and/or phosphorylation site(s), or those designed to delete an existing glycosylation and/or phosphorylation site(s). Variants include at least one amino acid substitution at a glycosylation site, a proteolytic cleavage site and/or a cysteine residue. Variants also include proteins and peptides with additional amino acid residues before or after the protein or peptide amino acid sequence on linker peptides. For example, a cysteine residue may be added at both the amino and carboxy terminals of FT in order to allow the cyclisation of the peptide by the formation of a di-sulphide bond. The term "variant" also encompasses polypeptides that have the amino acid sequence of FT with at least one and up to 25 or more additional amino acids flanking either the 3' or 5' end of the peptide.

The term "derivative" refers to a chemically modified protein or polypeptide that has been chemically modified either by natural processes, such as processing and other post-translational modifications, but also by chemical modification techniques, as for example, by addition of one or more polyethylene glycol molecules, sugars, phosphates, and/or other such molecules, where the molecule or molecules are not naturally attached to wild-type proteins or FT. Derivatives include salts. Such chemical modifications are well described in basic texts and in more detailed monographs, as well as in a voluminous research literature, and they are well known to those of skill in the art. It will be appreciated that the same type of modification may be present in the same or varying degree at several sites in a given protein or polypeptide. Also, a given protein or polypeptide may contain many types of modifications. Modifications can occur anywhere in a protein or polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, Proteins—Structure And Molecular Properties, 2nd Ed., T. E. Creighton, W. H. Freeman and Company, New York (1993) and Wold, F., "Posttranslational Protein Modifications: Perspectives and Prospects," pgs. 1-12 in Posttranslational Covalent Modification Of Proteins, B. C. Johnson, Ed., Academic Press, New York (1983); Seifter et al., Meth. Enzymol. 182:626-646 (1990) and Rattan et al., "Protein Synthesis: Posttranslational Modifications and Aging," Ann. N.Y. Acad. Sci. 663: 48-62 (1992). The term "derivatives" include chemical modifications resulting in the protein or polypeptide becoming branched or cyclic, with or without branching. Cyclic, branched and branched circular proteins or polypeptides may result from post-translational natural processes and may be made by entirely synthetic methods, as well.

The term "homologue" refers to a protein that is at least 60 percent identical in its amino acid sequence of FT as determined by standard methods that are commonly used to compare the similarity in position of the amino acids of two polypeptides. The degree of similarity or identity between two proteins can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M Stockton Press, New York, 1991; and Carillo H. and Lipman, D., SIAM, J. Applied Math., 48:1073 (1988). Preferred methods to determine identity are designed to give the largest match between the sequences tested. Methods to determine identity and similarity are codified in publicly available computer programs.

Preferred computer program methods useful in determining the identity and similarity between two sequences include, but are not limited to, the GCG program package (Devereux, J., et al., Nucleic Acids Research, 12(1): 387 (1984)), BLASTP, BLASTN, and FASTA, Atschul, S. F. et al., J. Molec. Biol., 215: 403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol., 215: 403-410 (1990). By way of example, using a computer algorithm such as GAP (Genetic Computer Group, University of Wisconsin, Madison, Wis.), the two proteins or polypeptides for which the percent sequence identity is to be determined are aligned for optimal matching of their respective amino acids (the "matched span", as determined by the algorithm).

A gap opening penalty (which is calculated as 3 times the average diagonal; the "average diagonal" is the average of the diagonal of the comparison matrix being used; the "diagonal" is the score or number assigned to each perfect amino acid match by the particular comparison matrix) and a gap extension penalty (which is usually {fraction (1/10)} times the gap opening penalty), as well as a comparison matrix such as PAM 250 or BLOSUM 62 are used in conjunction with the algorithm. A standard comparison matrix (see Dayhoff et al. in: Atlas of Protein Sequence and Structure, vol. 5, supp.3 for the PAM250 comparison matrix; see Henikoff et al., Proc. Natl. Acad. Sci USA, 89:10915-10919 for the BLOSUM 62 comparison matrix) also may be used by the algorithm. The percent identity then is calculated by the algorithm. Homologues will typically have one or more amino acid substitutions, deletions, and/or insertions as compared with the comparison protein or peptide, as the case may be.

The term "fusion protein" refers to a protein where one or more peptides are recombinantly fused or chemically conjugated (including covalently and non-covalently) to a protein such as (but not limited to) an antibody or antibody fragment like an Fab fragment or short chain Fv. The term "fusion protein" also refers to multimers (i.e. dimers, trimers, tetramers and higher multimers) of peptides. Such multimers comprise homomeric multimers comprising one peptide, heteromeric multimers comprising more than one peptide, and heteromeric multimers comprising at least one peptide and at least one other protein. Such multimers may be the result of hydrophobic, hyrdrophilic, ionic and/or covalent associations, bonds or links, may be formed by cross-links using linker molecules or may be linked indirectly by, for example, liposome formation The term "peptide mimetic" or "mimetic" refers to biologically active compounds that mimic the biological activity of a peptide or a protein but are no longer peptidic in chemical nature, that is, they no longer contain any peptide bonds (that is, amide bonds between amino acids). Here, the term peptide mimetic is used in a broader sense to include molecules that are no longer completely peptidic in nature, such as pseudo-peptides, semi-peptides and peptoids. Examples of peptide mimetics in this broader sense (where part of a peptide is replaced by a structure lacking peptide bonds) are described below. Whether completely or partially non-peptide, peptide mimetics according to the embodiments provide a spatial arrangement of reactive chemical moieties that closely resemble the three-dimensional arrangement of active groups in the peptide on which the peptide mimetic is based. As a result of this similar active-site geometry, the peptide mimetic has effects on biological systems that are similar to the biological activity of the peptide.

The peptide mimetics of the embodiments are preferably substantially similar in both three-dimensional shape and biological activity to the peptides described herein. Examples of methods of structurally modifying a peptide known in the art to create a peptide mimetic include the inversion of backbone chiral centers leading to D-amino acid residue structures that may, particularly at the N-terminus, lead to enhanced stability for proteolytical degradation without adversely affecting activity. An example is given in the paper "Tritriated D-ala.sup.1-Peptide T Binding", Smith C. S. et al., Drug Development Res., 15, pp. 371-379 (1988). A second method is altering cyclic structure for stability, such as N to C interchain imides and lactames (Ede et al. in Smith and Rivier (Eds.) "Peptides: Chemistry and Biology", Escom, Leiden (1991), pp. 268-270). An example of this is given in conformationally restricted thymopentin-like compounds, such as those disclosed in U.S. Pat. No. 4,457,489 (1985), Goldstein, G. et al., the disclosure of which is incorporated by reference herein in its entirety. A third method is to substitute peptide bonds in the peptide by pseudopeptide bonds that. confer resistance to proteolysis.

A number of pseudopeptide bonds have been described that in general do not affect peptide structure and biological activity. One example of this approach is to substitute retro-inverso pseudopeptide bonds ("Biologically active retroinverso analogues of thymopentin", Sisto A. et al in Rivier, J. E. and Marshall, G. R. (eds) "Peptides, Chemistry, Structure and Biology", Escom, Leiden (1990), pp. 722-773) and Dalpozzo, et al. (1993), Int. J. Peptide Protein Res., 41:561-566, incorporated herein by reference). According to this modification, the amino acid sequences of the peptides may be identical to the sequences of an peptide described above, except that one or more of the peptide bonds are replaced by a retro-inverso pseudopeptide bond. Preferably the most N-terminal peptide bond is substituted, since such a substitution will confer resistance to proteolysis by exopeptidases acting on the N-terminus. Further modifications also can be made by replacing chemical groups of the amino acids with other chemical groups of similar structure. Another suitable pseudopeptide bond that is known to enhance stability to enzymatic cleavage with no or little loss of biological activity is the reduced isostere pseudopeptide bond (Couder, et al. (1993), Int. J. Peptide Protein Res., 41:181-184, incorporated herein by reference in its entirety).

Thus, the amino acid sequences of these peptides may be otherwise identical to the sequence of FT, except that one or more of the peptide bonds are replaced by an isostere pseudopeptide bond. Preferably the most N-terminal peptide bond is substituted, since such a substitution would confer resistance to proteolysis by exopeptidases acting on the N-terminus. The synthesis of peptides with one or more reduced isostere pseudopeptide bonds is known in the art (Couder, et al. (1993), cited above). Other examples include the introduction of ketomethylene or methylsulfide bonds to replace peptide bonds.

Peptoid derivatives of peptides represent another class of peptide mimetics that retain the important structural determinants for biological activity, yet eliminate the peptide bonds, thereby conferring resistance to proteolysis (Simon, et al., 1992, Proc. Natl. Acad. Sci. USA, 89:9367-9371, incorporated herein by reference in its entirety). Peptoids are oligomers of N-substituted glycines. A number of N-alkyl groups have been described, each corresponding to the side chain of a natural amino acid (Simon, et al. (1992), cited above). Some or all of the amino acids of the peptides may be replaced with the N-substituted glycine corresponding to the replaced amino acid.

The term "peptide mimetic" or "mimetic" also includes reverse-D peptides and enantiomers as defined below.

The term "reverse-D peptide" refers to a biologically active protein or peptide consisting of D-amino acids arranged in a reverse order as compared to the L-amino acid sequence of an peptide. Thus, the carboxy terminal residue of an L-amino acid peptide becomes the amino terminal for the D-amino acid peptide and so forth. For example, the peptide, ETESH (SEQ ID NO :2), becomes $H_d S_d E_d T_d E_d$, where $E_d$, $H_d$, $S_d$, and $T_d$ are the D-amino acids corresponding to the L-amino acids, E, H, S, and T respectively.

The term "enantiomer" refers to a biologically active protein or peptide where one or more the L-amino acid residues in the amino acid sequence of an peptide is replaced with the corresponding D-amino acid residue(s).

A "composition" as used herein, refers broadly to any composition containing an antibiotic and, optionally FT. The composition may comprise a dry formulation, an aqueous solution, or a sterile composition. Compositions that optionally include FT may be employed as hybridization probes. The probes may be stored in freeze-dried form and may be associated with a stabilizing agent such as a carbohydrate. In hybridizations, the probe may be deployed in an aqueous solution containing salts, e.g., NaCl, detergents, e.g., sodium dodecyl sulfate (SDS), and other components, e.g., Denhardt's solution, dry milk, salmon sperm DNA, etc.

This disclosure also is premised in part on the discovery that the use of antibiotics either alone or in combination with FT are capable of treating and/or ameliorating the symptoms of BPH, and provides an unexpected improvement in mean IPSS scores that is comparable to, and better than current FDA-approved oral medications for BPH. While not intending on being bound by any particular theory or operation, the inventor unexpectedly discovered that the administration of antibiotics, alone or in combination with FT, dramatically improved symptoms in patients suffering from BPH, and dramatically improved urinary peak flow rate.

Any antibiotic, or combinations thereof, may be used in the embodiments. It is preferred that the composition include a suitable antibiotic to prevent or reduce the incidence of bacterial infection that may be associated with urinary tract infections. Antibiotics used should provide adequate protection against the commonly encountered bacterial strains of uropathogens including: *Escherichia coli, Streptococcus faecalis, Proteus/Pseudomonas* spp. and coagulase-positive *Staphylococcus*. In an embodiment, the method encompasses administration of one, two, three or more antibiotics in the same or different formulation, and by the same or different administrative route. Antibiotics used in the embodiments may be selected from one or more of erythromycin, kitasamycin, streptomycin cephalothin, cephazolin, tetracycline, gramicidin, griseofulvin, gentamicin, novobiocin, ampicillin, imipenem, metronidazole, ceftriaxone, cephalexin, ciprofloxacin, gemifloxacin, fosfomycin, levofloxacin, moxifloxacin, norfloxacin, nitrofurantoin, ofloxacin, trimethoprim/sulfamethoxaxole, and derivatives and salts of any of the foregoing. The antibiotics also may be selected from one or more of ampicillin, gentamicin, imipenem, cephalothin, metronidazole, ciprofloxacin, gemifloxacin, fosfomycin, levofloxacin, moxifloxacin, norfloxacin, nitrofurantoin, and ofloxacin. The antibiotics may be administered in two or three different courses, including a course of a fluoroquinolone antibiotic, a course of metronidazole, and an intramuscular injection of an antibiotic selected from imepenem, gentamicin, and cephalothin.

Patients treated with the compositions described herein exhibited a dramatic improvement in the International Prostate Symptom Score (IPSS), when compared to administering a control, and when compared to the mean improvement in IPSS of 3-5 for currently available FDA-approved oral medications for BPH (see, e.g., McConnell, J D et al., "The effect of finasteride on the risk of acute urinary retention . . . ", *NEJM, Vol.* 338, pp. 557-63 (1998); Roehrborn, C G et al., "The effects of combination therapy with dutasteride and tumsulosin on . . . ," *Eur Urol., November;* 58(5):801 (2010)). The embodiments may result in a mean improvement in IPSS within the first year, within the range of from about 4 to about 8 points, or from about 5 to about 7 points, or from about 6 to about 7 points. When compared to the mean improvement in IPSS for currently available FDA-approved medications for BPH, administration of antibiotics provided a greater improvement in the mean IPSS by an amount of from about 20% to about 300%, or from about 25% to about 200% or from about 30% to about 150% during the first year. When compared to the mean improvement in IPSS for placebo alone (reported as between about 1.5 and 3 points after 90 days and between about 1 and 1.5 points at 1 year), administration of antibiotics provided a greater improvement in the mean IPSS by an amount of from about 50% to about 600%, or from about 75% to about 500% or from about 90% to about 350% during the first year.

The embodiments may result in a mean improvement in IPSS after 42 months, within the range of from about 2 to about 6 points, or from about 3 to about 5 points, or from about 4 to about 5 points. When compared to the mean improvement in IPSS for currently available FDA-approved medications for BPH (reported as from about 2-4), administration of antibiotics provided a greater improvement in the mean IPSS by an amount of from about 0% to about 200%, or from about 0% to about 150% or from about 0% to about 100% after 42 months. These results are truly unexpected, especially when the use of antibiotics had never previously been described as being useful or effective in treating BPH. The fact that the use of antibiotics is as effective, and in many cases far more effective than conventional oral medications is a surprising discovery. When compared to the mean improvement in IPSS for placebo alone (reported as between about 1 and 2 points after 42 months), administration of antibiotics provided a greater improvement in the mean IPSS by an amount of from about 50% to about 400%, or from about 75% to about 350% or from about 100% to about 300% after 42 months.

Patients treated with the compositions described herein also exhibited an improvement in the urinary peak flow rate (Qmax) in men suffering from BPH. The embodiments may result in a mean improvement in Qmax within the first year, within the range of from about 1 to about 4, or from about 1.3 to about 3.0, or from about 1.5 to about 2.5, or from about 1.75 to about 2.0. When compared to the improvement in Qmax for currently available FDA-approved medications for BPH (reported as between about 0.8 and 2.2 after 90 days and between about 1.5 and 2.2 at 1 year), administration of antibiotics provided anywhere from a slight decrease of about 15% to an improvement of about 150%, or an improvement of about 130%, or an improvement of about 50%, during the first year. When compared to the mean improvement in Qmax for placebo alone (reported as between about 0.5 to 0.8), administration of antibiotics provided a greater improvement in Qmax by an amount of from about 75% to about 350%, or from about 100% to about 325% or from about 125% to about 300% during the first year.

The embodiments include a method of treating a mammal suffering from BPH, comprising administering once or more than once at least one antibiotic to the mammal, either alone or in combination with administration of FT. The method includes, but is not limited to, administering a composition comprising the antibiotic orally, intramuscularly, intravenously, intraperitoneally, intracerebrally (intraparenchymally), intracerebroyentricularly, intralesionally, intraocularly, intraarterially, intrathecally, intratumorally, intranasally, topically, transdermally, subcutaneously, or intradermally, either alone or conjugated to a carrier. In one embodiment, mammals may receive a course of a broad spectrum antibiotic (typically 7 days) such as a fluoroquinolone antibiotic, a course (typically 7 days) of an antibiotic such as metronidazole, and an intramuscular injection of a third broad spectrum antibiotic such as imipenen, gentamicin, or cephalothin.

In some embodiments, administration of fluoroquinolones such as Ciprofloxacin or Levofloxacin (and the like) may include orally administering from about 300 to about 600 mg, or from about 400 to about 550 mg, or 500 mg, twice daily for about 5 to about 10 days, or more. Administration of metronidazole, or Secnidazole, or Tinidazole, may include orally administering from about 300 to about 600 mg, or from about 400 to about 550 mg, or 500 mg, three times daily for about 5 to about 10 days, or more. Administration of Gentamicin and the like may include administering by intramuscular injection from about 50 to about 200 mg, or from about 75 to about 150 mg, or 100 mg, once daily for two or more days. Administration of Primaxin (Imipenem), or Invanz (Ertapenem) and the like, may include administering by intramuscular injection from about 0.1 to about 5 g, or from about 0.5 to about 1.5 g, or 1 g, once daily for one or more days. Those skilled in the art will be capable of determining a suitable amount of antibiotic, depending on the type of antibiotic, and using the guidelines provided herein.

The co-administration of FT with the antibiotics can result in an additional mean improvement in IPSS of from about 1.0 to about 5.0 points, or from about 1.2 to about 3.5 points, or from about 1.5 to about 3.0 points. Accordingly, if the mean improvement in IPSS from administration of antibiotics was about 6.2, then the mean improvement in IPSS from administration of a combination of antibiotic and FT would be from about 7.2 to about 11.2 points. The mean improvement in IPSS from administration of a combination of antibiotic and FT can be from about 5.0 to about 13.0 points, or from about 6.0 to about 11.0 points, or from about 7.5 to about 9.0 points, or from about 8.0 to about 9.0 points.

Any mammal can benefit from use of the invention, including humans, mice, rabbits, dogs, sheep and other livestock, any mammal treated or treatable by a veterinarian, zoo-keeper, or wildlife preserve employee. Preferred mammals are humans, sheep, and dogs. Throughout this description mammals and patients are used interchangeably.

It will be apparent to one of skill in the art that other smaller fragments of FT may be selected such that these peptides will possess the same or similar biological activity. Other fragments of may be selected by one skilled in the art such that these peptides will possess the same or similar biological activity. The peptides of the embodiments encompass these other fragments. In general, the peptides of the embodiments have at least 4 amino acids, preferably at least 5 amino acids, and more preferably at least 6 amino acids.

FT and fragments, variants, derivatives, homologues, fusion proteins and mimetics thereof encompassed by this embodiment can be prepared using methods known to those of skill in the art, such as recombinant DNA technology, protein synthesis and isolation of naturally occurring peptides, proteins, variants, derivatives and homologues thereof. FT and fragments, variants, derivatives, homologues, fusion proteins and mimetics thereof can be prepared from other peptides, proteins, and fragments, variants, derivatives and homologues thereof using methods known to those having skill in the art. Such methods include (but are not limited to) the use of proteases to cleave the peptide, or protein into FT. Any method disclosed in, for example, U.S. Pat. Nos. 6,924,266; 7,241,738; 7,317,077; 7,408,021; 7,745,572; 8,067,378; 8,293,703; 8,569,446; and 8,716,247, and U.S. Patent Application Publication Nos. 2017/0360885; 2017/0020957; 2016/0361380; and 2016/0215031, can be used to prepare the FT peptide described herein.

An additional embodiment includes administration of a composition comprising one or more antibiotics, optionally FT, and optionally, and additional active agent. The additional active agent, if used, can be one or more active agents selected from (i) anti-cancer active agents (such as alkylating agents, topoisomerase I inhibitors, topoisomerase II inhibitors, RNA/DNA antimetabolites, and antimitotic agents); (ii) active agents for treating benign growths such as anti-acne and anti-wart active agents (salicylic acid); (iii) antiandrogen compounds, (cyproterone acetate (1α, 2ß-methylene-6-chloro-17 α-acetoxy-6-dehydroprogesterone)) Tamoxifen, aromatase inhibitors); (iv) alphal-adrenergic receptor blockers (tamsulosin, terazosin, doxazosin, prazosin, bunazosin, indoramin, alfulzosin, silodosin); (v) 5α-reductase inhibitors (finasteride, dutasteride); (vi) phosphodiesterase type 5 (PDE5) inhibitors (tadalafil) and combinations thereof. Preferably, the additional active agent is selected from the group consisting of tamsulosin, finasteride, terazosin, doxazosin, prazosin, tadalafil, alfuzosin, silodosin, dutasteride, combinations of dutasteride and tamsulosin, and mixtures and combinations thereof.

Therapeutic compositions described herein may comprise a therapeutically effective amount of one or more antibiotics in admixture with a pharmaceutically acceptable carrier. In some alternative embodiments, the FT and/or additional active agent(s) can be administered in the same composition with the antibiotic, and in other embodiments, the composition comprising the one or more antibiotics is administered orally (gel, capsule, tablet, liquid, etc.), and a separate composition comprising one or more antibiotics is administered as an injection. Optionally, FT is administered in the form of a composition comprising the purified FT peptide in conjunction with one or more physiologically acceptable carriers, excipients, or diluents. Neutral buffered saline or saline mixed with serum albumin are exemplary appropriate carriers. Preferably, the product is formulated as a lyophilizate using appropriate excipients (e.g., sucrose). Other standard carriers, diluents, and excipients may be included as desired. Optionally, the additional active agent(s) can be administered orally (gel, capsule, tablet, liquid, etc). Compositions of the embodiments also may comprise buffers known to those having ordinary skill in the art with an appropriate range of pH values, including Tris buffer of about pH 7.0-8.5, or acetate buffer of about pH 4.0-5.5, which may further include sorbitol or a suitable substitute therefor.

Solid dosage forms for oral administration include but are not limited to, capsules, tablets, pills, powders, and granules. In such solid dosage forms, the antibiotic, and optionally FT and/or an additional active agent, can be admixed with at least one of the following: (a) one or more inert excipients (or carrier), such as sodium citrate or dicalcium phosphate; (b) fillers or extenders, such as starches, lactose, sucrose, glucose, mannitol, and silicic acid; (c) binders, such as carboxymethylcellulose, alginates, gelatin, polyvinylpyrrolidone, sucrose and acacia; (d) humectants, such as glycerol; (e) disintegrating agents, such as agar-agar, calcium carbonate, potato or tapioca starch, alginic acid, certain complex silicates, and sodium carbonate; (f) solution retarders, such as paraffin; (g) absorption accelerators, such as quaternary ammonium compounds; (h) wetting agents, such as acetyl alcohol and glycerol monostearate; (i) adsorbents, such as kaolin and bentonite; and (j) lubricants, such as talc, calcium stearate, magnesium stearate, solid polyethylene glycols, sodium lauryl sulfate, or mixtures thereof. For capsules, tablets, and pills, the dosage forms may also comprise buffering agents.

Liquid dosage forms for oral administration include pharmaceutically acceptable emulsions, solutions, suspensions, syrups, and elixirs. In addition to the active compounds, the liquid dosage forms may comprise inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, oils, such as cottonseed oil, groundnut oil, corn germ oil, olive oil, castor oil, and sesame oil, glycerol, tetrahydrofurfuryl alcohol, polyethyleneglycols, fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

Actual dosage levels of active ingredients in the compositions of the embodiments may be varied to obtain an amount of antibiotic, optional FT and optional additional active agent that is effective to obtain a desired therapeutic response for a particular composition and method of administration. The selected dosage level therefore depends upon the desired therapeutic effect, the route of administration, the desired duration of treatment, and other factors.

With mammals, including humans, the effective amounts can be administered on the basis of body surface area. The interrelationship of dosages for animals of various sizes, species and humans (based on mg/M$^2$ of body surface) is described by E. J. Freireich et al., Cancer Chemother. Rep., 50 (4):219 (1966). Body surface area may be approximately determined from the height and weight of an individual (see e.g., Scientific Tables, Geigy Pharmaceuticals, Ardsley, N.Y. pp. 537-538 (1970)).

The total daily dose of the antibiotic, optional FT peptide, and optional and additional active agent administered to a host may be in single or divided doses. Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, potency of the administered drug, rates of absorption and excretion, combination with other drugs and the severity of the particular disease being treated.

In certain embodiments, the at least one optional active agent can be selected from the group consisting of (1) of an inhibitor of 5α-reductase and/or an antiestrogen, (2) an inhibitor of 5α-reductase and/or an aromatase inhibitor, (3) a 5α-reductase inhibitor and/or a 17β-HSD inhibitor, (4) a 5α-reductase inhibitor, an antiestrogen and an aromatase inhibitor, (5) a 5α-reductase inhibitor, an antiestrogen and a 17β-HSD inhibitor, (6) a 5α-reductase inhibitor, an aromatase inhibitor, an antiestrogen and a 17β-HSD inhibitor, (7) a 5α-reductase inhibitor, an antiandrogen and an antiestrogen, (8), a 5α-reductase inhibitor, an antiandrogen and an aromatase inhibitor, (9) a 5α-reductase inhibitor, an antiandrogen and an 17β-HSD inhibitor, (10) a 5α-reductase inhibitor, an antiandrogen, an antiestrogen and an aromatase inhibitor, (11) a 5α-reductase inhibitor, an antiandrogen, an aromatase inhibitor and a 17β-HSD inhibitor, (12) a 5α-reductase inhibitor, an antiandrogen, an aromatase inhibitor, an antiestrogen and a 17β-HSD inhibitor, (13) a 17β-HSD inhibitor and an antiestrogen, (14) a 17β-HSD inhibitor and an aromatase inhibitor, (15) a 17β-HSD inhibitor, an aromatase inhibitor and an antiestrogen, (16) a 17β-HSD inhibitor, an antiandrogen and an antiestrogen, (17) a 17β-HSD inhibitor, an antiandrogen and an aromatase inhibitor, (18) a 17β-HSD inhibitor, an antiandrogen, an antiestrogen and an aromatase inhibitor, (19) an antiestrogen and an aromatase inhibitor and (20) an antiestrogen, an aromatase inhibitor, and an antiandrogen, (21) an LHRH agonist or antagonist, an inhibitor of 5α-reductase and an antiestrogen, (22) an LHRH agonist or antagonist, an inhibitor of 5α-reductase and an aromatase inhibitor, (23) an LHRH agonist or antagonist, a 5α reductase inhibitor and a 17β-HSD inhibitor, (24) an LHRH agonist or antagonist, a 5α-reductase inhibitor, an antiestrogen and an aromatase inhibitor, (25) an LHRH agonist or antagonist, a 5α-reductase inhibitor, an antiestrogen and a 17β-HSD inhibitor, (26) an LHRH agonist or antagonist, a 5α-reductase inhibitor, an aromatase inhibitor, an antiestrogen and a 17β-HSD inhibitor, (27) an LHRH agonist or antagonist, a 5α-reductase inhibitor, an antiandrogen and an antiestrogen, (28), an LHRH agonist or antagonist, a 5α-reductase inhibitor, an antiandrogen and an aromatase inhibitor, (29) an LHRH agonist or antagonist, a 5α-reductase inhibitor, an antiandrogen and an 17β-HSD inhibitor, (30) an LHRH agonist or antagonist, a 5α-reductase inhibitor, an antiandrogen, an antiestrogen and an aromatase inhibitor, (31) an LHRH agonist or antagonist, a 5α-reductase inhibitor, an antiandrogen, an aromatase inhibitor and a 17β-HSD inhibitor, (32) an LHRH agonist or antagonist, a 5α-reductase inhibitor, an antiandrogen, an aromatase inhibitor, an antiestrogen and a 17β-HSD inhibitor, (33) an LHRH agonist or antagonist, a 17β-HSD inhibitor and an antiestrogen, (34) an LHRH agonist or antagonist, a 17β-HSD inhibitor and an aromatase inhibitor, (35) an LHRH agonist or antagonist, a 17β-HSD inhibitor, an aromatase inhibitor and an antiestrogen, (36) an LHRH agonist or antagonist, a 17β-HSD inhibitor, an antiandrogen and an antiestrogen, (37) an LHRH agonist or antagonist, a 17β-HSD inhibitor, an antiandrogen and an aromatase inhibitor, (38) an LHRH agonist or antagonist, a 17β-HSD inhibitor, an antiandrogen, an antiestrogen and an aromatase inhibitor, (39) an LHRH agonist or antagonist, an antiestrogen and an aromatase inhibitor and (40) an LHRH agonist or antagonist, an antiestrogen, an aromatase inhibitor, and an antiandrogen.

The following examples are provided to illustrate the present embodiments. It should be understood, however, that the embodiments are not to be limited to the specific conditions or details described in these examples. Throughout the specification, any and all references to a publicly available document, including a U.S. patent, are specifically incorporated by reference. In particular, the embodiments expressly incorporate by reference the examples contained in U.S. Pat. Nos. 6,924,266; 7,241,738; 7,317,077; 7,408,021; 7,745,572; 8,067,378; 8,293,703; 8,569,446; and 8,716,247, and U.S. Patent Application Publication Nos. 2017/0360885; 2017/0020957; 2016/0361380; and 2016/0215031.

Example One

In a study of 977 men, patients with BPH were given an intraprostatic injection of either a) NX-1207 in phosphate buffered saline pH 7.2 ("PBS") or b) PBS alone, under double-blind conditions by a urologist in an office setting under ultrasound guidance. Prior to the drug or placebo treatments, each patient started a course of broad spectrum antibiotics consisting of 7 days of a fluoroquinolone antibiotic, 7 days of metronidazole and an intramuscular injection of a third broad spectrum antibiotic such as imipenem or gentamicin or cephalothin. Each patient was followed for one year or longer with regular physical examinations, laboratory tests, and evaluations of symptoms. Symptomatic evaluation was measured by the International Prostate Symptom Score (IPSS) which is a quantitative scale used to gauge prostatic symptomatic improvement or worsening. The IPSS quantifies the following: 1) incomplete bladder emptying after urination; 2) frequent urination; 3) stopping and starting during urination; 4) urgent need to urinate; 5) weakness of urinary stream; 6) need to push or strain during urination; 7) need to urinate after going to sleep at night (nocturia). The difference from baseline IPSS was compared in patients who were given NX-1207 vs patients who received PBS alone. Surprisingly it was found after 90 days that patients who received only antibiotics plus placebo had an improvement in their BPH symptom scores that were superior to what is normally found with oral conventional BPH medications. The results are summarized in Table 4.

TABLE 4

| Treatment | Number of patients | Duration after treatment | Mean Improvement (points) |
|---|---|---|---|
| Placebo plus antibiotics | 391 | 90 days | 6.7 [7.02] |
| Conventional oral BPH drug treatment | | 90 days | 3-5* |

*based on published reports. [x] indicates standard deviation

As shown in Table 4, patients treated with one or more antibiotics provided a mean improvement in IPSS ranging from about 34% to about 123%, when compared to conventional oral BPH drug treatments, when measured 90 days after treatment. Administration of one or more antibiotics therefore provides a greater mean improvement in IPSS in patients suffering from BPH, than the FDA approved oral medications for treating BPH. This improvement is unexpected in light of the fact that antibiotics were not previously known to have any effect, or any significant effect on treating BPH.

Example Two

In a study of 977 men, patients with BPH were given an intraprostatic injection of either a) NX-1207 in phosphate buffered saline pH 7.2 ("PBS") or b) PBS alone, under double-blind conditions by a urologist in an office setting under ultrasound guidance. Prior to the drug or placebo treatments, each patient started a course of broad spectrum antibiotics consisting of 7 days of a fluoroquinolone antibiotic, 7 days of metronidazole and an intramuscular injection of a third broad spectrum antibiotic such as imipenem or gentamicin or cephalothin. Each patient was followed for one year or longer with regular physical examinations, laboratory tests, and evaluations of symptoms. Symptomatic evaluation was measured by the International Prostate Symptom Score (IPSS) which is a quantitative scale used to gauge prostatic symptomatic improvement or worsening. The IPSS quantifies the following: 1) incomplete bladder emptying after urination; 2) frequent urination; 3) stopping and starting during urination; 4) urgent need to urinate; 5) weakness of urinary stream; 6) need to push or strain during urination; 7) need to urinate after going to sleep at night (nocturia). The difference from baseline IPSS was compared in patients who were given NX-1207 vs patients who received PBS alone. Surprisingly it was found after 12 months that patients who received only antibiotics plus placebo had an improvement in their BPH symptom scores that were superior to what is normally found with oral conventional BPH medications. The results are summarized in Table 5.

TABLE 5

| Treatment | Number of patients | Duration after treatment | Mean Improvement (points) |
|---|---|---|---|
| Placebo plus antibiotics | 391 | 1 year | 6.2 [7.09] |
| Conventional oral BPH drug treatment | | 1 year | 2-4* |

*based on published reports. [x] indicates standard deviation

The results of Table 5 show that patients treated with one or more antibiotics provided a mean improvement in IPSS ranging from about 55% to about 210%, when compared to conventional oral BPH drug treatments, when measured 1 year after treatment. Administration of one or more antibiotics therefore provides a greater mean improvement in IPSS in patients suffering from BPH, than the FDA approved oral medications for treating BPH. This improvement is unexpected.

Example Three

In a study of 977 men, patients with BPH were given an intraprostatic injection of either a) NX-1207 in phosphate buffered saline pH 7.2 ("PBS") or b) PBS alone, under double-blind conditions by a urologist in an office setting under ultrasound guidance. Prior to the drug or placebo treatments, each patient started a course of broad spectrum antibiotics consisting of 7 days of a fluoroquinolone antibiotic, 7 days of metronidazole and an intramuscular injection of a third broad spectrum antibiotic such as imipenem or gentamicin or cephalothin. Each patient was followed for one year or longer with regular physical examinations, laboratory tests, and evaluations of symptoms. Urinary peak flow rate (Qmax) is a measurement performed in a flow meter that outputs the maximum urinary flow rate as recorded electronically in mL/second. Qmax was compared in patients who were given NX-1207 vs patients who received PBS alone. Surprisingly it was found after 3 months that patients who received only antibiotics plus placebo had an improvement in their maximum urinary flow rates that were comparable to or better to what is normally found with oral conventional BPH medications. The results are summarized in Table 6.

TABLE 6

| Treatment | Number of patients | Duration after treatment | Mean Improvement |
|---|---|---|---|
| Placebo + antibiotics | 391 | 3 months | +1.9 [4.65] |
| Conventional oral BPH drug treatments | | 3 months | +0.8-2.2* |

*based on reported values in the literature, not corrected for drop-outs treated as failures. [x] denotes standard deviation.

The results of Table 6 show that patients treated with one or more antibiotics provided a mean improvement in Qmax comparable to or better than what is normally found in conventional medications. After 3 months, administration of one or more antibiotics provided a mean improvement in Qmax, when compared to conventional BPH oral drug treatments, ranging from about −13% to about 137%.

Example Four

In a study of 977 men, patients with BPH were given an intraprostatic injection of either a) NX-1207 in phosphate buffered saline pH 7.2 ("PBS") or b) PBS alone, under double-blind conditions by a urologist in an office setting under ultrasound guidance. Prior to the drug or placebo treatments, each patient started a course of broad spectrum antibiotics consisting of 7 days of a fluoroquinolone antibiotic, 7 days of metronidazole and an intramuscular injection of a third broad spectrum antibiotic such as imipenem or gentamicin or cephalothin. Each patient was followed for one year or longer with regular physical examinations, laboratory tests, and evaluations of symptoms. Urinary peak flow rate (Qmax) is a measurement performed in a flow meter that outputs the maximum urinary flow rate as recorded electronically. Qmax was compared in patients who were given NX-1207 vs patients who received PBS alone. Surprisingly it was found after 12 months that patients who received only antibiotics plus placebo had an improvement in their maximum urinary flow rates that were comparable to what is normally found with oral conventional BPH medications. The results are summarized in Table 7.

TABLE 7

| Treatment | Number of patients | Duration after treatment | Mean Improvement |
|---|---|---|---|
| Placebo + antibiotics | 391 | 1 year | +1.9 [4.64] |
| Conventional oral BPH drug treatments | | 1 year | +1.5-2.2* |

*based on reported values in the literature, not corrected for drop-outs treated as failures. [x] denotes standard deviation.

The results of Table 7 show that patients treated with one or more antibiotics provided a mean improvement in Qmax comparable to or better than what is normally found in conventional medications. After 1 year, administration of one or more antibiotics provided a mean improvement in Qmax, when compared to conventional BPH oral drug treatments, ranging from about −13% to about 27%.

Example Five

In a study of 977 men, patients with BPH were given an intraprostatic injection of either a) NX-1207 in phosphate buffered saline pH 7.2 ("PBS") or b) PBS alone, under double-blind conditions by a urologist in an office setting under ultrasound guidance. Prior to the drug or placebo treatments, each patient started a course of broad spectrum antibiotics consisting of 7 days of a fluoroquinolone antibiotic, 7 days of metronidazole and an intramuscular injection of a third broad spectrum antibiotic such as imipenem or gentamicin or cephalothin. Each patient was followed for one year or longer with regular physical examinations, laboratory tests, and evaluations of symptoms. Symptomatic evaluation was measured by the International Prostate Symptom Score (IPSS) which is a quantitative scale used to gauge prostatic symptomatic improvement or worsening. The IPSS quantifies the following: 1) incomplete bladder emptying after urination; 2) frequent urination; 3) stopping and starting during urination; 4) urgent need to urinate; 5) weakness of urinary stream; 6) need to push or strain during urination; 7) need to urinate after going to sleep at night (nocturia). The difference from baseline IPSS was compared in patients who were given NX-1207 vs patients who received PBS alone. Surprisingly it was found after 90 days that patients who received only antibiotics plus placebo had an improvement in their BPH symptom scores that were superior to what is normally found in BPH trials with oral placebo alone. The results are summarized in Table 8.

TABLE 8

| Treatment | Number of patients | Duration after treatment | Mean Improvement (points) |
|---|---|---|---|
| Placebo plus antibiotics | 391 | 90 days | 6.7 [7.02] |
| Placebo alone | | 90 days | 1.5-3* |

*based on published reports. [x] indicates standard deviation

As shown in Table 8, patients treated with one or more antibiotics provided a mean improvement in IPSS ranging from about 123% to about 350%, when compared to placebo alone, when measured 90 days after treatment. Administration of one or more antibiotics therefore provides a greater mean improvement in IPSS in patients suffering from BPH, than the FDA approved oral medications for treating BPH. This improvement is unexpected.

Example Six

In a study of 977 men, patients with BPH were given an intraprostatic injection of either a) NX-1207 in phosphate buffered saline pH 7.2 ("PBS") or b) PBS alone, under double-blind conditions by a urologist in an office setting under ultrasound guidance. Prior to the drug or placebo treatments, each patient started a course of broad spectrum antibiotics consisting of 7 days of a fluoroquinolone antibiotic, 7 days of metronidazole and an intramuscular injection of a third broad spectrum antibiotic such as imipenem or gentamicin or cephalothin. Each patient was followed for one year or longer with regular physical examinations, laboratory tests, and evaluations of symptoms. Symptomatic evaluation was measured by the International Prostate Symptom Score (IPSS) which is a quantitative scale used to gauge prostatic symptomatic improvement or worsening. The IPSS quantifies the following: 1) incomplete bladder emptying after urination; 2) frequent urination; 3) stopping and starting during urination; 4) urgent need to urinate; 5) weakness of urinary stream; 6) need to push or strain during urination; 7) need to urinate after going to sleep at night (nocturia). The difference from baseline IPSS was compared in patients who were given NX-1207 vs patients who received PBS alone. Surprisingly it was found after 12 months that patients who received only antibiotics plus placebo had an improvement in their BPH symptom scores that were superior to what is normally found in BPH trials with oral placebo alone The results are summarized in Table 9.

TABLE 9

| Treatment | Number of patients | Duration after treatment | Mean Improvement (points) |
|---|---|---|---|
| Placebo plus antibiotics | 391 | 1 year | 6.2 [7.09] |
| Placebo alone | | 1 year | 1-1.5* |

*based on published reports. [x] indicates standard deviation

The results of Table 9 show that patients treated with one or more antibiotics provided a mean improvement in IPSS ranging from about 313% to about 520%, when compared to placebo alone, when measured 1 year after treatment. Administration of one or more antibiotics therefore provides a greater mean improvement in IPSS in patients suffering from BPH, than the FDA approved oral medications for treating BPH. This improvement is unexpected.

Example Seven

In a study of 977 men, patients with BPH were given an intraprostatic injection of either a) NX-1207 in phosphate buffered saline pH 7.2 ("PBS") or b) PBS alone, under double-blind conditions by a urologist in an office setting under ultrasound guidance. Prior to the drug or placebo treatments, each patient started a course of broad spectrum antibiotics consisting of 7 days of a fluoroquinolone antibiotic, 7 days of metronidazole and an intramuscular injection of a third broad spectrum antibiotic such as imipenem or gentamicin or cephalothin. Each patient was followed for one year or longer with regular physical examinations, laboratory tests, and evaluations of symptoms. Urinary peak flow rate (Qmax) is a measurement performed in a flow meter that outputs the maximum urinary flow rate as recorded electronically. Qmax was compared in patients who were given NX-1207 vs patients who received PBS alone. Surprisingly it was found after 3 months that patients who received only antibiotics plus placebo had an improvement in their maximum urinary flow rates that were superior to what is normally found in BPH trials with oral placebo alone. The results are summarized in Table 10.

TABLE 10

| Treatment | Number of patients | Duration after treatment | Mean Improvement |
|---|---|---|---|
| Placebo + antibiotics | 391 | 3 months | +1.9 [4.65] |
| Placebo alone | | 3 months | +0.5-0.8* |

*based on reported values in the literature, not corrected for drop-outs treated as failures.
[x] denotes standard deviation.

The results of Table 10 show that patients treated with one or more antibiotics provided a mean improvement in Qmax comparable to or better than what is normally found in conventional medications. After 3 months, administration of one or more antibiotics provided a mean improvement in Qmax, when compared to a control placebo alone, ranging from about 138% to about 280%.

Example Eight

In a study of 977 men, patients with BPH were given an intraprostatic injection of either a) NX-1207 in phosphate buffered saline pH 7.2 ("PBS") or b) PBS alone, under double-blind conditions by a urologist in an office setting under ultrasound guidance. Prior to the drug or placebo treatments, each patient started a course of broad spectrum antibiotics consisting of 7 days of a fluoroquinolone antibiotic, 7 days of metronidazole and an intramuscular injection of a third broad spectrum antibiotic such as imipenem or gentamicin or cephalothin. Each patient was followed for one year or longer with regular physical examinations, laboratory tests, and evaluations of symptoms. Urinary peak flow rate (Qmax) is a measurement performed in a flow meter that outputs the maximum urinary flow rate as recorded electronically. Qmax was compared in patients who were given NX-1207 vs patients who received PBS alone. Surprisingly it was found after 12 months that patients who received only antibiotics plus placebo had an improvement in their maximum urinary flow rates that were superior to what is normally found in BPH trials with oral placebo alone. The results are summarized in Table 11.

TABLE 11

| Treatment | Number of patients | Duration after treatment | Mean Improvement |
|---|---|---|---|
| Placebo + antibiotics | 391 | 1 year | +1.9 [4.64] |
| Placebo alone | | 1 year | +0.5-0.8* |

*based on reported values in the literature, not corrected for drop-outs treated as failures. [x] denotes standard deviation.

The results of Table 11 show that patients treated with one or more antibiotics provided a mean improvement in Qmax superior to what is normally found in BPH trials with oral placebo alone. After 1 year, administration of one or more antibiotics provided a mean improvement in Qmax, when compared to a control placebo alone, ranging from about 138% to about 280%.

Example Nine

In a study of 977 men, patients with BPH were given an intraprostatic injection of either a) NX-1207 in phosphate buffered saline pH 7.2 ("PBS") or b) PBS alone, under double-blind conditions by a urologist in an office setting under ultrasound guidance. Prior to the drug or placebo treatments, each patient started a course of broad spectrum antibiotics consisting of 7 days of a fluoroquinolone antibiotic, 7 days of metronidazole and an intramuscular injection of a third broad spectrum antibiotic such as imipenem or gentamicin or cephalothin. Each patient was followed for one year or longer with regular physical examinations, laboratory tests, and evaluations of symptoms. Symptomatic evaluation was measured by the International Prostate Symptom Score (IPSS) which is a quantitative scale used to gauge prostatic symptomatic improvement or worsening. The IPSS quantifies the following: 1) incomplete bladder emptying after urination; 2) frequent urination; 3) stopping and starting during urination; 4) urgent need to urinate; 5) weakness of urinary stream; 6) need to push or strain during urination; 7) need to urinate after going to sleep at night (nocturia). The difference from baseline IPSS was compared in patients who were given NX-1207 vs patients who received PBS alone. Surprisingly it was found after long-term (mean 42 months) that patients who received only antibiotics plus placebo had an improvement in their BPH symptom scores that were comparable or superior to what is normally found with oral conventional BPH medications. The results are summarized in Table 12.

TABLE 12

| Treatment | Number of patients | Duration after treatment | Mean Improvement (points) |
|---|---|---|---|
| Placebo plus antibiotics | 391 | 42 months | 4.0 [6.03] |
| Conventional oral BPH drug treatment | | 1 year | 2-4* |

*based on published reports. [x] indicates standard deviation

The results of Table 12 show that patients treated with one or more antibiotics provided a mean improvement in IPSS ranging from about 0% to about 100%, when compared to conventional oral BPH drug treatments, when measured 42 months after treatment. Administration of one or more antibiotics therefore provides a mean improvement in IPSS in patients suffering from BPH comparable or superior to what is normally found with oral conventional BPH medications. This result is unexpected.

Example Ten

In a study of 977 men, patients with BPH were given an intraprostatic injection of either a) NX-1207 in phosphate buffered saline pH 7.2 ("PBS") or b) PBS alone, under double-blind conditions by a urologist in an office setting under ultrasound guidance. Prior to the drug or placebo treatments, each patient started a course of broad spectrum antibiotics consisting of 7 days of a fluoroquinolone antibiotic, 7 days of metronidazole and an intramuscular injection of a third broad spectrum antibiotic such as imipenem or gentamicin or cephalothin. Each patient was followed for one year or longer with regular physical examinations, laboratory tests, and evaluations of symptoms. Symptomatic evaluation was measured by the International Prostate Symptom Score (IPSS) which is a quantitative scale used to gauge prostatic symptomatic improvement or worsening. The IPSS quantifies the following: 1) incomplete bladder emptying after urination; 2) frequent urination; 3) stopping and starting during urination; 4) urgent need to urinate; 5) weakness of urinary stream; 6) need to push or strain during urination; 7) need to urinate after going to sleep at night (nocturia). The difference from baseline IPSS was compared in patients who were given NX-1207 vs patients who received PBS alone. Surprisingly it was found after long-term (mean 42 months) that patients who received only antibiotics plus placebo had an improvement in their BPH symptom scores that were superior to what is normally found with oral placebo alone. The results are summarized in Table 13.

TABLE 13

| Treatment | Number of patients | Duration after treatment | Mean Improvement (points) |
|---|---|---|---|
| Placebo plus antibiotics | 391 | 42 months | 4.0 [6.03] |
| Placebo alone | | 42 months | 1-2* |

*based on published reports. [x] indicates standard deviation

The results of Table 13 show that patients treated with one or more antibiotics provided a mean improvement in IPSS ranging from about 100% to about 300%, when compared to placebo alone, when measured 42 months after treatment. Administration of one or more antibiotics therefore provides a greater mean improvement in IPSS in patients suffering from BPH, than were superior to what is normally found with oral placebo alone.

The published reports referred to in the tables above include one or more of the following: McConnell, J D et al., "The effect of finasteride on the risk of acute urinary retention . . . ", *NEJM*, Vol. 338, pp. 557-63 (1998); Roehrborn, C G et al., "The effects of combination therapy with dutasteride and tumsulosin on . . . ," *Eur Urol.*, November; 58(5):801 (2010); Lukacs, B et al., "Managament of Lower Urinary Tract Symptoms Related to . . . " *Eur Urol.*, February; 64; pp 493-501 (2013); and Cindolo, L et al., "Drug Adherence and Clinical Outcomes for Patients Under Pharmacological Therapy for . . . " *Eur Urol., February;* 68; pp 418-425 (2015).

The results from the foregoing examples illustrate the unexpectedly superior effect of the use of antibiotics in improving IPSS and Qmax in patients suffering from BPH. It will be apparent to those skilled in the art that various modifications and variations can be made in the methods and compositions of the present embodiments without departing from the spirit or scope of the embodiments.

What is claimed is:

1. A method of improving the symptoms of mammals suffering from BPH comprising administering to the mammal a composition comprising a therapeutically effective amount of one or more antibiotics, wherein the antibiotics are administered by administration of a course of a fluoroquinolone antibiotic, a course of metronidazole, and an intramuscular injection of an antibiotic selected from imipenem, gentamicin, and cephalothin.

2. The method of claim 1, wherein the fluoroquinolone antibiotic is selected from the group consisting of ciprofloxacin, gemifloxacin, fosfomycin, levofloxacin, moxifloxacin, norfloxacin, ofloxacin, and derivatives and salts of any of the foregoing.

3. The method of claim 2, wherein the fluoroquinolone antibiotic is selected from ciprofloxacin and levofloxacin.

4. The method of claim 1, further comprising improving the International Prostate Symptom Score (IPSS) by lowering the mean IPSS from baseline by from 5 to 7 points, within one year.

5. The method of claim 1, further comprising improving the mean IPSS score, when compared to the mean improvement in mean IPSS from oral medications for BPH, by an amount within the range of from about 30% to about 150% during the first year.

6. The method of claim 1, further comprising improving the mean IPSS score, when compared to a placebo control, by an amount within the range of from about 75% to about 500% during the first year.

7. The method of claim 1, further comprising improving the International Prostate Symptom Score (IPSS) by lowering the mean IPSS from baseline by from 4 to 5 points, within 42 months.

8. The method of claim 1, further comprising improving the mean IPSS score, when compared to the mean improvement in mean IPSS from oral medications for BPH, by an amount within the range of from about 0% to about 200% within 42 months.

9. The method of claim 1, further comprising improving the mean IPSS score, when compared to a placebo control, by an amount within the range of from about 75% to about 350% within 42 months.

10. The method of claim 1, further comprising improving the urinary peak flow rate (Qmax) by increasing the maximum urinary flow by an amount within the range of from about 1.3 to about 3.0 ml/sec within the first year.

11. The method of claim 1, further comprising improving the mean Qmax, when compared to a placebo control, by an amount within the range of from about 100% to about 325% during the first year.

12. The method of claim 1, further comprising administration of Fexapotide Triflutate and a pharmaceutically acceptable carrier.

13. The method of claim 12, wherein Fexapotide Triflutate is administered by a route selected from the group consisting of intramuscularly, orally, intravenously, intrathecally, intratumorally, intranasally, topically, and transdermally.

14. The method of claim 1, further comprising administration of a pharmaceutically active agent selected from the group consisting of tamsulosin, finasteride, terazosin, doxazosin, prazosin, tadalafil, alfuzosin, silodosin, dutasteride, combinations of dutasteride and tamsulosin, and mixtures and combinations thereof.

15. The method of claim 12, further comprising administration of a pharmaceutically active agent selected from the group consisting of tamsulosin, finasteride, terazosin, doxazosin, prazosin, tadalafil, alfuzosin, silodosin, dutasteride, combinations of dutasteride and tamsulosin, and mixtures and combinations thereof.

\* \* \* \* \*

```
SEQUENCE LISTING

<160> NUMBER OF SEQ ID NOS: 2

<210> SEQ ID NO 1
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ile Asp Gln Gln Val Leu Ser Arg Ile Lys Leu Glu Ile Lys Arg Cys
1               5                   10                  15

Leu

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Glu Thr Glu Ser His
1               5
```